United States Patent [19]

Rabinovich et al.

[11] 4,399,051

[45] Aug. 16, 1983

[54] METHOD FOR REGENERATION OF RHODIUM-CONTAINING CATALYST

[76] Inventors: Georgy L. Rabinovich, ulitsa Antonova-Ovseenko, 19, korpus 2, kv. 14; Zoya P. Lukina, Manezhny pereulok, 2, kv. 2; Kira L. Volkova, ulitsa Antonova-Ovseenko, 19, korpus 2, kv. 4, all of Leningrad; Viktor N. Mozhaiko, ulitsa Nevskaya, 3, kv. 3, Otradnoe Leningradskoi oblasti, all of U.S.S.R.

[21] Appl. No.: 237,150
[22] PCT Filed: May 5, 1980
[86] PCT No.: PCT/SU80/00073
   § 371 Date: Feb. 17, 1981
   § 102(e) Date: Feb. 17, 1981
[87] PCT Pub. No.: WO80/02809
   PCT Pub. Date: Dec. 24, 1980

[30] Foreign Application Priority Data

Jun. 15, 1979 [SU] U.S.S.R. ............................. 2770904

[51] Int. Cl.$^3$ .................. B01J 23/96; B01J 21/04; C07C 4/18; C07C 15/06
[52] U.S. Cl. .................. 252/415; 252/411 S; 252/412; 585/486; 585/489
[58] Field of Search ............... 252/411 S, 411 R, 412, 252/415, 420; 585/487; 208/140

[56] References Cited

U.S. PATENT DOCUMENTS

| | | | |
|---|---|---|---|
| 2,225,782 | 12/1940 | Ipatieff et al. | 252/411 S |
| 3,117,076 | 1/1964 | Brennan et al. | 208/140 |
| 3,440,007 | 4/1969 | Takevichi et al. | 252/412 |
| 4,139,433 | 2/1979 | Ward | 252/412 |
| 4,228,033 | 10/1980 | Yamauchi et al. | 252/411 S |

FOREIGN PATENT DOCUMENTS

| | | | |
|---|---|---|---|
| 49-86329 | 8/1974 | Japan | |
| 52-107428 | 3/1977 | Japan | 252/411 S |
| 229477 | 2/1972 | U.S.S.R. | |
| 348033 | 5/1972 | U.S.S.R. | |
| 448671 | 3/1978 | U.S.S.R. | |
| 627849 | 8/1978 | U.S.S.R. | |

*Primary Examiner*—P. E. Konopka
*Attorney, Agent, or Firm*—Lilling & Greenspan

[57] ABSTRACT

A method for regenerating of rhodium-containing catalysts exhausted and sulphur-poisoned in the course of dealkylating alkyl benzenes or mixture thereof with steam or hydrogen, comprising the steps of burning out coke deposits by an oxygen-containing gas and chlorinating the catalyst with chlorine or with a chlororganic compound in a flow of hydrogen, an inert gas or a mixture of an inert gas with oxygen and moisture. The catalyst is additionally treated with ammonia or with a nitrogen-containing compound capable of decomposing under the treatment to yield ammonia in the presence of at least one component selected from the group consisting of: water, hydrogen, and nitrogen-oxygen mixture. The treatment can be conducted both in the liquid and the gaseous phases at temperatures ranging between 20° and 650° C. and at a pressure between 1 and 50 atm.

The present invention can be used for regeneration of rhodium-containing catalysts and used for dealkylating alkyl benzenes with steam or hydrogen.

8 Claims, No Drawings

METHOD FOR REGENERATION OF RHODIUM-CONTAINING CATALYST

FIELD OF THE INVENTION

The present invention relates to petrochemical processing, and more particularly, to methods for regeneration of rhodium-containing catalysts. The invention is particularly concerned with methods for regeneration of rhodium-containing catalysts for dealkylating alkyl benzenes.

DESCRIPTION OF THE PRIOR ART

Known in the prior art is a method for dealkylating alkyl benzenes by conversion with steam. The known method seeks to obtain aromatic hydrocarbons with less molecular weight than that of alkyl aromatic hydrocarbons contained in a raw material. Dealkylation of toluene for example proceeds as follows:

$$C_6H_5CH_3 + 2H_2O \rightarrow C_6H_6 + CO_2 + 3H_2$$

$$C_6H_5CH_3 + H_2O \rightarrow C_6H_6 + CO + 2H_2$$

The process is carried out at a temperature of from 400° to 500° C. and at a pressure up to 30 atm using individual alkyl aromatic hydrocarbons or their mixtures with hydrocarbons of other classes as a raw material. Dealkylation of aromatic hydrocarbons with steam is carried out using catalysts containing noble metals of Group VIII of the Periodic System, preferably rhodium, applied to alumina (Cf. USSR Inventor's Certificate No. 229,477, Int. Cl. CO7c 15/04, published Mar. 22, 1972).

To increase activity, selectivity and stability of the rhodium/alumina catalyst, alkali metals, alkaline-earth metals as well as metals belonging to the group of copper, ferrum, chrome and lanthanum are introduced into the catalyst composition (Cf. British Pat. No. 1,313,941, Int. Cl. CO7c 3/58, patented Apr. 18, 1973; U.S. Pat. Nos. 3,436,433 and 3,436,434, Int. Cl. CO7c 3/58, BO1j 21/04, patented Apr. 1, 1969; U.S. Pat. Nos. 3,649,706 and 3,649,707, Int. Cl. CO7c 3/58, BO1j 21/04, patented Mar. 14, 1972; U.S. Pat. No. 3,848,014, Int. Cl. CO7c 3/58 patented Nov. 12, 1974).

Rhodium-containing catalysts are also used to conduct the reaction of dealkylation with hydrogen (hydrodealkylation).

$$C_6H_5CH_3 + H_2 \rightarrow C_6H_6 + CH_4$$

Under conditions of dealkylation, the activity of the rhodium-containing catalysts drops. Therefore, the process is carried out by alternating reaction cycles with that of regeneration. The processes influencing a decline in activity of the catalyst are still not clearly understood. Some of them are due to carbon deposits on the catalyst surface and a decline in specific surface of rhodium due to agglomeration of its crystals.

Known in the prior art is a method for regeneration of a rhodium-alumina catalyst, residing in purging it with either hydrogen or a mixture of hydrogen with steam at a temperature of from 300° to 550° C. and pressure up to 20 atm (Cf. USSR Inventor's Certificate No. 348,033, Int. Cl. BO1j 11/68, published Mar. 5, 1978). The above method makes it possible to reclaim the catalyst activity provided the length of the reaction period does not exceed 100–120 hours. Moreover, it is not possible to reclaim the catalyst activity if the dealkylation process is carried out under severe conditions (over 480° C.).

Also known in the art is a method for regenerating a rhodium-containing catalyst, residing in treating it with either a nitrogen-oxygen mixture or air-steam mixture in order to burn out coke, followed by chlorination at a temperature between 400° and 600° C. with a nitrogen-oxygen mixture containing 0.1 to 0.2 g/l of chlorine or a chlororganic compound. The catalyst is then reclaimed in a flow of hydrogen at a temperature of from 450° to 550° C. followed by treatment of the catalyst with steam at a temperature of from 400° to 500° C. and further using it in the process of dealkylation (Cf. USSR Inventor's Certificate No. 448,671, Int. Cl. BO1j 11/58, published Mar. 15, 1978).

Activity of the regenerated catalyst increases in case a chlorine-containing gaseous mixture used in the chlorination stage contains, in addition, water vapour in an amount of 0.002 to 0.1 g/l (Cf. USSR Inventor's Certificate No. 627,849, Int. Cl. BO1j 11/68, published Oct. 15, 1978).

However, the rhodium-containing catalyst regeneration by means of carbon-burning-out or chlorination is efficient only in case the latter has not undergone sulphur poisoning. Sulphur is the strongest poison for dealkylation catalysts. The catalyst life is only 2.5 hours if sulphur content in a raw material amounts to 52 ppm (Cf. Japanese Application No. 7486329, published Aug. 19, 1974). Sulphur results in irreversible poisoning of the catalyst leaving no possibility to reduce its activity by any known methods of regeneration. Hydrocarbons or water used in reactions involves impurities of sulphur-containing compounds. It is very difficult to prevent a catalyst from being poisoned in a reaction cycle since in practice it is not possible to remove sulphur from a raw material completely, in a rather long reaction cycle a catalyst tends to be sulphur poisoned even though there are only negligible quantities of sulphur in a raw material. Sulphur removal (desulphuration) from rhodium-containing catalysts is a much more difficult problem compared with that of platinum-containing catalysts used in hydrocarbon conversions. Whereas a platinum rhenium catalyst requires treatment only with hydrogen at a temperature of from 350° to 600° C. and pressure up to 50 atm in order to provide sulphur removal therefrom (Cf. Australian Pat. No. 454,135, Int. Cl. BO1j, patented Oct. 4, 1974) such a procedure for a rhodium-containing catalyst does not yield any appreciable sulphur reduction in said catalyst. Presumably rhodium reacts with sulphur to form especially stable compounds requiring other treatment conditions for their decomposition.

The absence of a method for regenerating a rhodium-containing catalyst poisoned by sulphur is the reason that the method of alkylbenzene dealkylation on these catalysts has not yet been put into operation on commercial scale.

SUMMARY OF THE INVENTION

The principal object of the present invention is to increase the life of rhodium-containing catalysts by treating sulphur-poisoned catalysts with reagents allowing for the removal of sulphur from the catalyst surface.

With this principal object in view, there is provided a method for regenerating rhodium-containing catalyst used for dealkylating alkyl benzenes by conversion with steam or hydrogen, comprising the steps of burning out carbon deposits by an oxygen-containing gas, chlorinating the catalyst with chlorine or with a chlororganic compound in a flow of hydrogen, an inert gas, or a mixture of an inert gas with oxygen and moisture, wherein, according to the invention, the catalyst is additionally treated at a temperature of from 20° to 650° C., at a pressure of 1 to 50 atm, during 0.5 to 48 hours with liquid ammonia in the form of an aqueous solution, or in the gaseous ammonia per se, or in the form of a nitrogen-containing compound capable of decomposing under said treatment to yield ammonia. The treatment with ammonia in the gaseous phase is conducted in the presence of at least one component selected from the group consisting of: water, hydrogen, or a nitrogen-oxygen mixture.

Sulphur removal from the sulphur-poisoned catalyst takes place after exposure of the rhodium-containing catalyst to ammonia. Interaction of rhodium sulphide with ammonia can conceivably be visualised as follows:

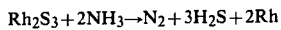
$Rh_2S_3 + 2NH_3 \rightarrow N_2 + 3H_2S + 2Rh$

This fact appears to be rather unexpected, since hydrogen being one of the most strong reductants does not actually react with rhodium sulphide and a reaction such as

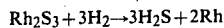
$Rh_2S_3 + 3H_2 \rightarrow 3H_2S + 2Rh$ does not proceed to any noticeable extent.

To achieve a more complete removal of sulphur from a catalyst a high content of ammonia is needed. Nevertheless it is desirable to get other than ammonia compounds in a gaseous mixture and this fact appeared to be also quite unexpected.

As gaseous mixture components in addition to ammonia, water or steam, hydrogen, and nitrogen-oxygen mixtures are used. Such compounds as ethanol form water and hydrogen on a catalyst in a process of dehydration and dehydrogenation can also be used.

Nitrogen-oxygen mixtures as noted herein can contain a different quantity of oxygen varying from technical nitrogen comprising usually 1% vol. of $O_2$ to air. Mixtures of oxygen with inert gases as well as with $CO_2$ can also be used. Instead of ammonia, some of compounds such as ammonium chloride, an alkylammonium compound, ethanolamine, hydroxylamine or a salt of hydroxylamine chlorhydrate, which form ammonia while decomposing can be used. The use of chlorine-containing compounds of ammonia makes it possible to combine the process of desulphuration of a catalyst with its chlorination.

The catalyst is treated with ammonia either in a gaseous or liquid state.

The catalyst treatment with ammonia is an essential stage in the regeneration process of the rhodium-containing dealkylation catalysts reducing their activity in a reaction cycle. To reclaim the initial activity of spent catalysts the regeneration process should include an ammonia treatment stage, carbon burning-out and chlorination. Such intermediate operations as catalyst reduction and calcination can be carried out between the operative steps.

The catalyst treatment with ammonia in the gaseous phase is carried out by passing ammonia together with steam, hydrogen, and a nitrogen-oxygen mixture through a catalyst. In the liquid phase it is convenient to treat a catalyst with aqueous ammonia. Ammonia treatment can be carried out in sequence varying with reference to other regeneration on stages.

For example:

(a) ammonia treatment, carbon burning-out, chlorination;

(b) carbon burning-out, chlorination, ammonia treatment;

(c) carbon burning-out, ammonia treatment, chlorination.

Under ammonia treatment, the degree of desulphuration increases with increasing temperature and pressure, however simultaneous action of high temperature (above 650° C.) and pressure (up to 50 atm), results in rapid rhodium sintering and reducing of the specific surface of a carrier. Therefore a gaseous phase treatment is carried out preferably at a temperature from 150° to 650° C. and pressure of between 5 and 15 atm.

According to the invention, ammonia treatment in combination with the above mentioned components is more effective than with ammonia alone. At the same time to achieve a more complete removal of sulphur, the ammonia concentration should be sufficiently high. It is preferable to use mixtures with an ammonia concentration of 20–95% vol.

Aqueous ammonia is used for treatment in a liquid phase. A rise in temperature favors more complete sulphur removal, but for liquid phase treatment at a temperature above 200° C., pressure above 15 atm is needed to the detriment of catalytic properties of a catalyst. Therefore, the preferable temperature interval for treatment ranges from room temperature to 200° C. It is possible to carry out ammonia treatment at a temperature lower than room temperature but it is inconvenient due to the necessity to cool the catalyst and solution used for treatment.

Under aqueous ammonia treatment at a temperature over 100° C., the pressure should vary from 1–15 atm, to ensure carrying out the treatment in a liquid phase.

The duration of ammonia treatment is governed by ammonia content. When using aqueous solutions or gaseous mixtures with a high content of ammonia, the treatment duration ranges from 0.5 to 5 hours. With highly concentrated solutions, the complete removal of sulphur can be achieved in a time of less than 0.5 hour, but this is technologically unwarranted. A decrease in ammonia content results in an increase of time necessary to remove sulphur from a catalyst up to 24–48 hours.

Ammonia concentration in aqueous solutions can vary in a wide range, from 0.01 mass % up to a saturated ammonia solution but it is preferable to use solutions having concentrations of 0.5–5 weight %.

Ammonia treatment can be carried out at any stage of regeneration, but it is advisable to treat catalysts wherein metallic components are in oxidized form, i.e. after the carbon burning-out stage or chlorination stage.

BEST MODE OF CARRYING OUT THE INVENTION

The process of dealkylation is carried out by passing alkyl benzenes or their mixtures with hydrocarbons of other classes and steam or hydrogen at a temperature of from 450° to 650° C. and at a pressure of 5–10 atm through a catalyst situated in a flow reactor.

While in operation, catalysts tend to reduce their activity. To maintain a constant benzene yield for the quantity of charge used the temperature rises gradually as catalyst activity decreases. On reaching the temperature responsible for reducing process selectivity (benzene yield on a converted charge), the reaction cycle comes to an end and the catalyst is to be regenerated. The regeneration cycle is carried out either directly in the reaction vessel for dealkylation or in a separate apparatus. The regeneration cycle involves burning-out coke deposits by an oxygen-containing inert gas, chlorinating step with chlorine or chlororganic compound in a flow of hydrogen, an inert gas or a mixture of an inert gas with oxygen and moisture, and an ammonia treatment stage. The sequence of the above mentioned stages can be varied and it is possible to carry out intermediate reduction or calcination of the catalyst after any of the operative steps. On finishing the regeneration cycle, the catalyst is reduced by hydrogen and reused in a process of dealkylation.

The advantages of the invention will be further described with reference to the following illustrative Examples.

EXAMPLE 1

A catalyst with decreased activity as a result of service for 2,000 hours in a process of toluene dealkylation with steam undergoes a regeneration cycle. The toluene that was used contained $4 \cdot 10^{-5}$ weight % of sulphur-containing compounds based on sulphur. The catalyst composition in % by weight is as follows: rhodium, 0.6; copper, 0.3; potassium, 2.5; the balance being alumina.

The catalyst testing procedure was carried out in a steel flow reactor 36 mm in diameter provided with a pocket for thermocouples 8 mm in diameter. 60 cm$^3$ of the catalyst were charged into the reactor and reduced with hydrogen fed at a rate of 100 l/h with a gradual increase (during 8 hours) in temperature up to 500° C., and held at this temperature for 2 hours. Upon termination of the reduction, a required testing temperature was set, whereupon toluene and water or toluene and hydrogen (in hydrodealkylation experiments) were fed into the reactor.

Liquid products were condensed in a cooler, whereupon gaseous products were separated in a gas separator. Product analysis was carried out by the gas chromatography method.

The process of dealkylation was carried out under the following conditions: pressure, 7 atm; space velocity of toluene feed, 1.3 h$^{-1}$; water-toluene molar ratio, 6.

At the starting period (24 hours) at 480° C. the benzene yield on toluene converted was 53.9 mass %, yield of the liquid product (toluene-benzene mixture) being 87.5 mass %. On finishing the experiment the benzene yield at the same temperature was reduced to 19 mass % provided the yield of the liquid product was 94.5 mass %.

In accordance with the analysis results, the catalyst was found to include 5.2 mass % of carbon deposits (coke) and 0.08 mass % of sulphur.

The regeneration process was carried out as follows. 60 cm$^3$ of the catalyst was treated directly in the reactor at 550° C. and a pressure of 30 atm with a mixture of ammonia, steam and hydrogen in the ratio of 1:2.5:6.5. To attain the objectives mentioned above an aqueous ammonia containing 28% ammonia, and hydrogen are passed through 60 cm$^3$ of the catalyst at a rate of 20 ml/h and 50 l/h, respectively. The duration of the treatment is 24 hours. Then the catalyst undergoes oxidative regeneration in order to burn-out coke. Coke burning-out was carried out at elevated temperatures ranging from 300° to 500° C. in a flow of nitrogen-oxygen mixture (technical nitrogen) containing 1% vol. of oxygen, space velocity of the feed mixture being 1,000 h$^{-1}$.

Chlorination of the catalyst was carried out in a quartz reactor 32 mm in diameter provided with a pocket for thermocouples 8 mm in diameter. The catalyst was heated to 550° C. in a flow of technical nitrogen. In the process of chlorination nitrogen was passed through a vessel with water up to moisture saturation, while chlorine obtained by electrolysis of an aqueous solution of sodium chlorite on platinum electrodes was supplied through a separate line. Steam-gas mixture containing 1% vol. of chlorine, 2% vol. of steam, 1% vol. of oxygen and the balance being nitrogen, was formed in the reactor. Space velocity of gas feed is 200 h$^{-1}$, and time of chlorination is 6 hours. Upon termination of the chlorination, the catalyst was cooled in a flow of nitrogen to room temperature, whereupon the catalyst was reloaded into a test unit for testing in the process of dealkylation. Before being tested the catalyst was reduced at 500° C. in a flow of hydrogen supplied at space velocity of 500 h$^{-1}$. The catalyst comprised 0.015 mass % of sulphur (sulphur content prior to regeneration cycle was 0.08 mass %).

In the process of toluene demethylation with steam under the above mentioned conditions using the regenerated catalyst, the yield in mass % of benzene for the quantity of toluene used was 53.5, while that of the liquid product was 87.6. The catalyst was practically regenerated completely.

EXAMPLE 2

(for comparison)

60 cm$^3$ of the spent catalyst similar to that of Example 1 underwent a regeneration cycle similar to that of Example 1 exluding desulphuration of the catalyst.

In the process of toluene demethylation with steam under conditions of Example 1 the yield of benzene in mass % was 21.5 and that of the liquid products was 94.0. The catalyst was not regenerated. In the treatment of the sulphur poisoned catalyst in a flow of hydrogen at 550° C. and a pressure of 30 atm for 24 hours the sulphur content expressed in mass % in the catalyst was only reduced from 0.08 to 0.065.

EXAMPLE 3

A catalyst was composed of the following components in mass %: rhodium, 0.6; ferrum, 2.0; potassium, 1.5; the balance being alumina. The catalyst was spent in the process of toluene demethylation with steam. Water used for dealkylation contained $7.5 \times 10^{-3}$ mass % of sulphuric acid.

Dealkylation conditions were the following: temperature, 520° C.; space velocity of toluene feed, 2.7 h$^{-1}$; water-toluene molar ratio 3, duration of the process with sulphur containing raw material, 24 hours. Yield in mass % of benzene toluene converted before sulphur poisoning was 61.2 and that of a liquid product, 84.0. Yield in mass % of benzene after sulphur poisoning of the catalyst was 17.3 and that of a liquid product was 95.0. Sulphur content in the catalyst was 0.1 mass %. 60 cm$^3$ of the catalyst underwent oxidative regeneration cycle in a flow of technical nitrogen (1% vol of O$_2$) at 500° C. Then 1,000 ml of aqueous ammonia with 5% of ammonia were passed at room temperature (20° C.) and atmospheric pressure through the catalyst for 3 hours. Thereon technical nitrogen (1% vol. of O$_2$) was passed through the catalyst, the temperature was increased to 500° C. and the catalyst was chlorinated by adding in nitrogen 2% vol. of moisture and 1% vol. of chlorine. The space velocity of the gaseous mixture feed was 200 h$^{-1}$. The duration of chlorination was 4 hours. Sulphur content in the regenerated catalyst was 0.01 mass %. The catalyst was reduced by hydrogen at 500° C. and then tested under conditions as those of a fresh catalyst based on a raw material free from sulphur. Yield in mass % of benzene for the quantity of toluene used was 62, while that of a liquid product was 84.6.

EXAMPLE 4

The sulphur poisoned catalyst with composition and conditions of poisoning similar to that of Example 3, underwent a regeneration cycle under conditions mentioned in Example 3 except for the desulphuration procedure which was carried out as follows. 1,200 ml of 0.01% aqueous solution of ammonia was passed through 60 cm$^3$ of the catalyst for 30 minutes. The residual quantity of sulphur was 0.025 mass %. While testing under conditions of Example 3, the yield in mass % of benzene was 40.4 and that of a liquid product was 92.3.

EXAMPLE 5

The catalyst (30 cm$^3$) comprising 0.3 mass % of rhodium and 0.3 mass % of platinum on an active aluminum oxide was tested in the reaction of toluene hydrodemethylation at atmospheric pressure, temperature of 510° C., space velocity of toluene feed 2.5 h$^{-1}$ and hydrogen-toluene molar ratio of 4. Under testing conditions the catalyst was poisoned by toluene contaminated by sulphur and containing 2·10$^{-2}$ mass. % of sulphur in the form of thiophene. The duration of the experiment was 8 hours. Yield in mass % of benzene on toluene converted before poisoning was 67, after poisoning, 21. Yields in mass % of liquid product were 84.1 and 94, respectively. Sulphur content in the catalyst was 0.08 mass %. After burning-out coke deposits at 500° C. by nitrogen-oxygen mixture (1% of O$_2$), the catalyst was chlorinated under conditions of Example 1 and then treated with a steam-gas mixture comprising water vapors, ammonia and air for 10 hours, with the molar ratio of ammonia:water vapor:air being 1:2.4:11. Space velocity of the steam-gas mixture feed was 900 h$^{-1}$, the treatment temperature was 150° C., pressure, 7 atm. Thereon the catalyst was reduced in a flow of hydrogen at 500° C. and tested in the hydrodemethylation reaction under the same conditions as those for a fresh catalyst. Benzene yield was 66.2 mass %, liquid product yield was 84.3 mass %.

EXAMPLE 6

A sample of the catalyst which was poisoned by sulphur as described in Example 5 underwent the regeneration cycle under conditions of Example 5 except for a desulphuration stage which was performed by passing dry ammonia alone at 150° C., a pressure of 7 atm and space velocity of ammonia feed of 900 h$^{-1}$ for 10 hours. Testing the catalyst in the hydrodemethylation process of toluene under conditions of Example 5 led to a benzene yield of 30 mass % and a liquid product yield of 94.0 mass %. The catalyst treatment by ammonia alone revealed a relatively poor effect of regeneration. An alike sample of the sulphur-poisoned catalyst was treated for 10 hours by a gaseous mixture comprising ammonia and steam in the ratio of 0.95:0.05 at 150° C. and at a pressure of 7 atm. The catalyst was thereon tested in the reaction of toluene hydromethylation under conditions of Example 5. The yield in mass % of benzene for the quantity of toluene used was 56.1 and that of a liquid product was 87.8.

EXAMPLE 7

The catalyst of Example 1 was regenerated. All procedures were the same as those of Example 1 except for the ammonia treatment stage. The above mentioned treatment was carried out at 650° C., a pressure of 50 atm for 48 hours under ammonia, steam and hydrogen in a ratio of 1:2.5:6.5. In testing under conditions of Example 1 the yield in mass % of benzene on treated toluene was 40.1 and that of a liquid product, 92.0. The regeneration cycle resulted only in a partial reduction of catalyst activity. The reason for an incomplete activity reduction of the catalyst was likely to relate to excessively severe conditions of the treatment.

EXAMPLE 8

Used as a raw material for dealkylation was a mixture of pyrolysis petroleum fractions, comprising in mass %: non-aromatic hydrocarbons, 4.6; benzene, 15.6; toluene, 65.2; aromatic hydrocarbons C$_8$, 6.6; aromatic hydrocarbons C$_9$, 8.0. The process of dealkylation of the above mentioned raw material was carried out on a fresh catalyst of Example 3 at 490° C., pressure of 7 atm, space velocity of the raw material feed of 1.3 h$^{-1}$, water-raw material mass ratio being 1.18. The experiments after sulphur poisoning of the catalyst as well as its regeneration were carried out under the conditions of Example 3.

Test results are given below in mass %.

|  | Yield | | Liquid product composition | | | | |
|---|---|---|---|---|---|---|---|
|  | benzene | liquid product | benzene | toluene | Ar C$_8$ | Ar C$_9$ | Nonaromatic hydrocarbons |
| Fresh catalyst | 46.7 | 85.8 | 54.5 | 39.3 | 3.3 | 1.2 | 1.4 |
| Poisoned catalyst | 18.0 | 96.1 | 18.9 | 66.0 | 7.1 | 4.1 | 3.9 |
| Regenerated catalyst | 48.7 | 85.1 | 57.2 | 36.1 | 3.2 | 2.0 | 1.2 |

COMMERCIAL APPLICABILITY

The herein-proposed method for regeneration can be employed on a commercial scale to reduce activity of rhodium-containing catalysts of alkyl benzene dealkylation process with steam and hydrogen.

The present invention makes it possible to provide reduction of a rhodium-containing catalyst with any promoter additions regardless the full composition of said catalyst. It is due to the fact that the present invention makes it possible to reduce the properties of rhodium which is an active component of the catalyst. The kind of sulphur-containing compounds in a raw material that caused catalyst poisoning is of no importance for the present invention.

We claim:

1. A method for regenerating a sulfur poisoned rhodium-containing catalyst used for dealkylating alkyl benzenes with steam or hydrogen, consisting essentially of the steps of: burning out carbon deposits with an oxygen-containing gas; chlorinating the catalyst, in a flow of gas selected from the group consisting of hydrogen, an inert gas, or a mixture of an inert gas with oxygen and moisture, with a chlorinating compound selected from the group consisting of chlorine or a chlororganic compound; and treating the catalyst at a temperature of from 20° to 650° C., and a pressure of from 1 to 50 atm, for 0.5 to 48 hours with a nitrogen-containing compound selected from the group consisting of an aqueous ammonia solution, gaseous ammonia, or a nitrogen-containing compound which decomposes under the treatment conditions to yield ammonia;

wherein the treatment with ammonia in the gaseous phase is conducted in the presence of at least one component selected from the group consisting of: steam, water, hydrogen, a nitrogen-oxygen mixture, and an oxygen-inert gas mixture.

2. A method according to claim 1, wherein the catalyst treatment with ammonia is carried out at any stage of the regeneration.

3. A method according to claim 1, wherein the ammonia treatment is carried out in the gaseous phase at a temperature of from 150° to 650° C. and a pressure of from 5 to 15 atm.

4. A method according to claim 3, wherein the catalyst is treated with ammonia gas having a concentration of 20 to 95% by volume.

5. A method according to claim 1, wherein the catalyst treatment is carried out with aqueous ammonia at a temperature of from 20° to 200° C. and a pressure of from 1 to 15 atm.

6. A method according to claim 5, wherein the catalyst treatment is carried out with aqueous ammonia concentrated to 0.5–5% by mass.

7. A method according to claim 5, wherein the catalyst treatment with aqueous ammonia is carried out after the step of burning out coke deposits or after the step of chlorination.

8. A method according to claim 1, wherein the rhodium-containing catalyst includes aluminum oxide.

* * * * *